(12) United States Patent
Abe et al.

(10) Patent No.: US 8,628,864 B2
(45) Date of Patent: Jan. 14, 2014

(54) INDOLO[3,2,1-JK]CARBAZOLE COMPOUND AND ORGANIC LIGHT-EMITTING DEVICE CONTAINING THE SAME

(75) Inventors: Shigemoto Abe, Yokohama (JP); Jun Kamatani, Tokyo (JP); Kengo Kishino, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 95 days.

(21) Appl. No.: 13/237,642

(22) Filed: Sep. 20, 2011

(65) Prior Publication Data
US 2012/0075273 A1   Mar. 29, 2012

(30) Foreign Application Priority Data

Sep. 29, 2010   (JP) .................................. 2010-219484

(51) Int. Cl.
*G06F 3/038* (2013.01)
*H01L 51/54* (2006.01)
*C07D 487/06* (2006.01)

(52) U.S. Cl.
USPC ..... 428/690; 548/419; 548/304.4; 548/305.1; 548/440; 546/276.7

(58) Field of Classification Search
None
See application file for complete search history.

(56) References Cited

U.S. PATENT DOCUMENTS

2005/0258744 A1* 11/2005 Kwak et al. ................... 313/504

FOREIGN PATENT DOCUMENTS

JP   2010-87496 A   4/2010
JP   2010087496 A * 4/2010

OTHER PUBLICATIONS

Machine English translation of JP 2010-087496 A. Mar. 13, 2013.*

* cited by examiner

*Primary Examiner* — Jennifer Chriss
*Assistant Examiner* — J. L. Yang
(74) *Attorney, Agent, or Firm* — Canon USA Inc. IP Division

(57) ABSTRACT

There is provided an indolo[3,2,1-jk]carbazole compound having an excellent membrane property, a high T1 energy, and a deep HOMO level. There is also provided an organic light-emitting device that contains the indolo[3,2,1-jk]carbazole compound.
There is provided an indolo[3,2,1-jk]carbazole compound having a high T1 energy and a deep HOMO level.

18 Claims, 1 Drawing Sheet

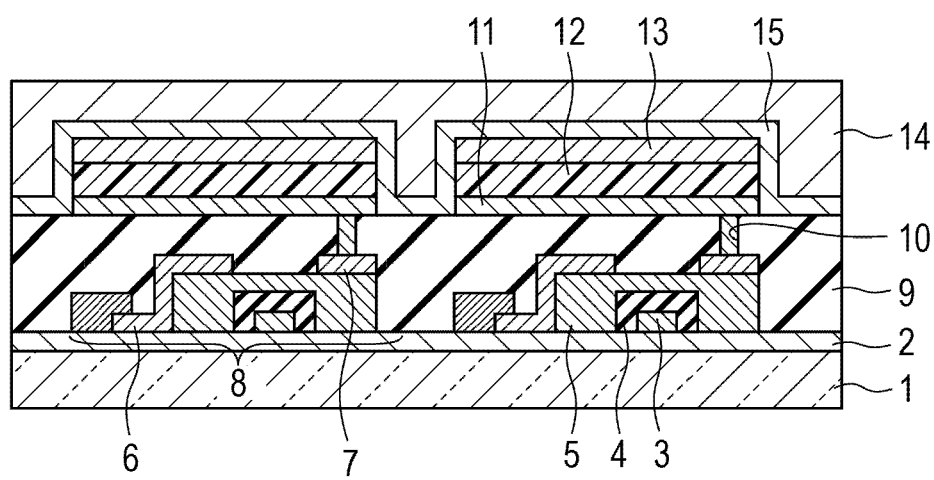

INDOLO[3,2,1-JK]CARBAZOLE COMPOUND AND ORGANIC LIGHT-EMITTING DEVICE CONTAINING THE SAME

BACKGROUND OF THE INVENTION

1. Field of the Invention

The present invention relates to an indolo[3,2,1-jk]carbazole compound and an organic light-emitting device containing the indolo[3,2,1-jk]carbazole compound.

2. Description of the Related Art

Organic light-emitting devices include an anode, a cathode, and an organic compound layer between the anode and the cathode. Positive holes (holes) and electrons from the electrodes recombine to form excitons in the organic compound layer. The organic light-emitting devices emit light while the excitons return to their ground state. Recent years have seen significant advances in organic light-emitting devices, resulting in light-emitting devices having a low driving voltage, various emission wavelengths, a high-speed responsivity, a low profile, and a light weight.

Phosphorescent devices are organic light-emitting devices containing phosphorescent materials in their organic compound layers and emit light caused by triplet excitons. There is room for improvement in the luminous efficiency of phosphorescent devices.

Japanese Patent Laid-Open No. 2010-87496 describes the following compounds FH-01 and FH-02 as materials for a light-emitting layer of a phosphorescent device.

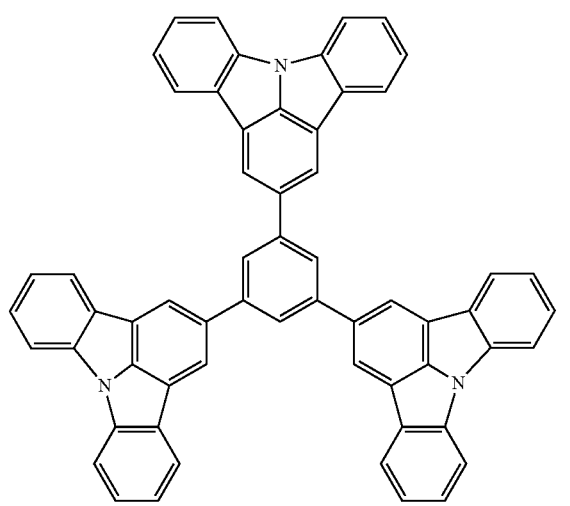

FH-01

FH-02

The compounds described in Japanese Patent Laid-Open No. 2010-87496 have high molecular planarity, high crystallinity, and consequently a low membrane property.

SUMMARY OF THE INVENTION

Aspects of the present invention provide an indolo[3,2,1-jk]carbazole compound having a high membrane property, a high T1 energy, and a deep HOMO level. Aspects of the present invention also provide an organic light-emitting device containing the indolo[3,2,1-jk]carbazole compound and having a high luminous efficiency and a low driving voltage.

Thus, aspects of the present invention provide an indolo[3,2,1-jk]carbazole compound represented by the following general formula [1].

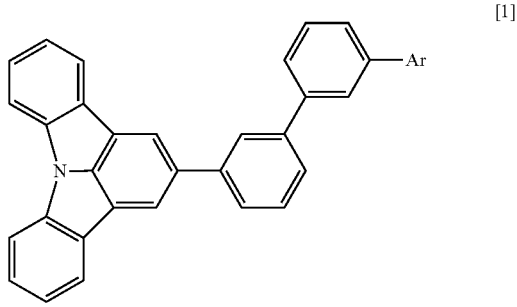

[1]

In the formula [1], Ar is selected from the substituents listed in the formula [2].

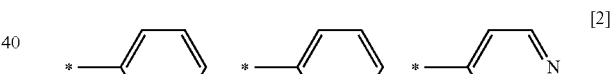

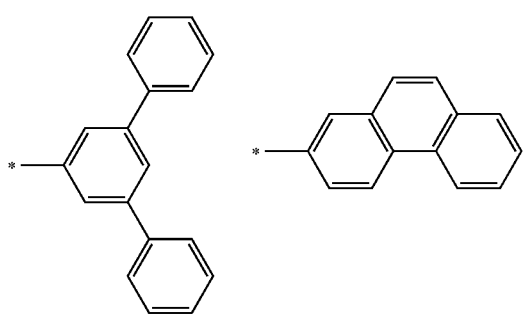

[2]

-continued

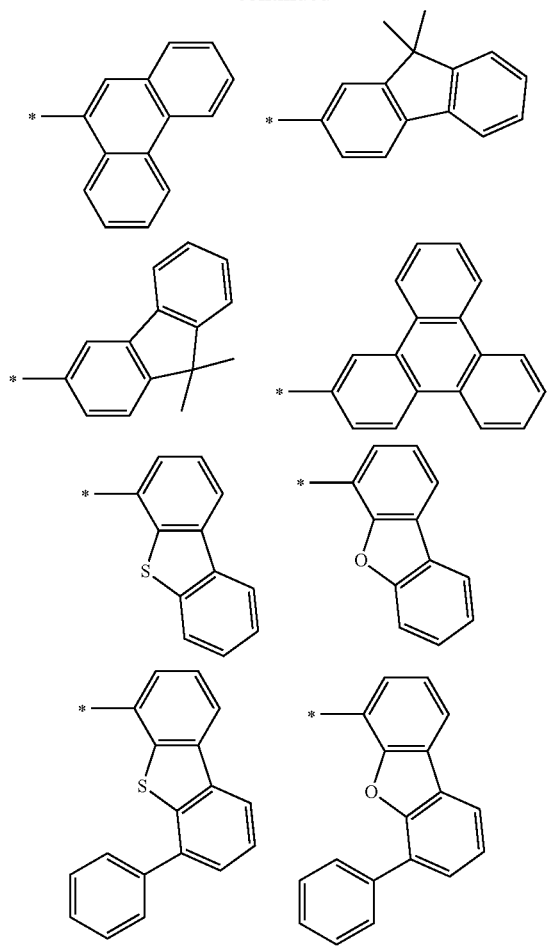

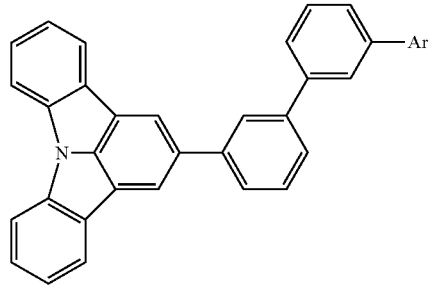

Ar in the formula [1] is selected from the substituents listed in the formula [2].

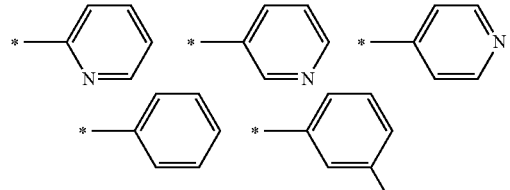

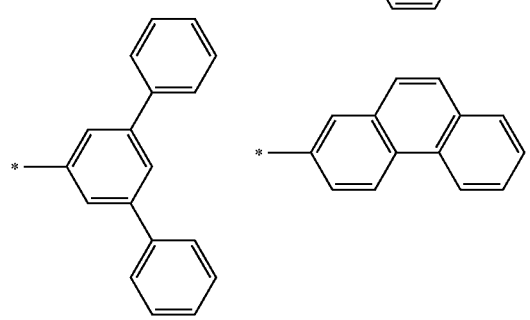

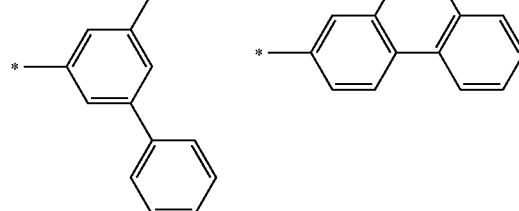

In the formula [2], * denotes a site to be bonded to the biphenyl group of the formula [1].

Aspects of the present invention can provide an indolo[3,2,1-jk]carbazole compound having an excellent membrane property, a high T1 energy, and a deep HOMO level. Aspects of the present invention can also provide an organic light-emitting device containing the indolo[3,2,1-jk]carbazole compound and having a high luminous efficiency and a low driving voltage.

Further features of the present invention will become apparent from the following description of exemplary embodiments with reference to the attached drawings.

BRIEF DESCRIPTION OF THE DRAWINGS

The FIGURE is a schematic cross-sectional view of an organic light-emitting device and a switching device, which is connected to the organic light-emitting device.

DESCRIPTION OF THE EMBODIMENTS

One embodiment according to aspects of the present invention is an indolo[3,2,1-jk]carbazole compound represented by the following general formula [1].

-continued

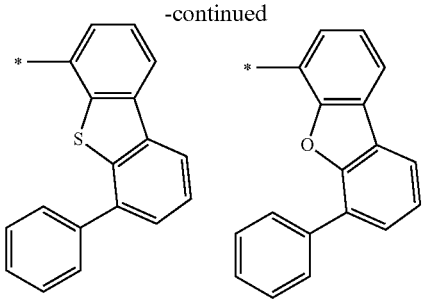

In the formula [2], * denotes a site to be bonded to the biphenyl group of the formula [1].

The indolo[3,2,1-jk]carbazole compound having the formula [1] is composed of an indolo[3,2,1-jk]carbazolyl group, a biphenyl group, and Ar.

The biphenyl group can reduce the crystallinity of the compound.

Since the indolo[3,2,1-jk]carbazolyl group has very high molecular planarity, compounds having a plurality of indolo[3,2,1-jk]carbazolyl groups have high crystallinity.

A compound according to an embodiment of the present invention has one biphenyl group per indolo[3,2,1-jk]carbazolyl group. The structure around the biphenyl group is made asymmetrical to achieve low crystallinity. The bonding between the indolo[3,2,1-jk]carbazolyl group or Ar and a meta position of the biphenyl group can reduce the crystallization of the compound, resulting in a high membrane property. The term "membrane property", as used herein, means that an amorphous state rather than a crystallized state is maintained.

In order to reduce crystallinity, the indolo[3,2,1-jk]carbazolyl group has no $sp^3$ carbon or silicon substituent. This is because the $sp^3$ carbon or silicon substituent reduces Tg. Furthermore, the $sp^3$ carbon or silicon substituent unfavorably facilitates oxidation, eliminates conjugation, and consequently separates molecular orbitals, reducing carrier transportability.

An organic light-emitting device made of a material having low carrier transportability may unfavorably have a significantly high driving voltage.

The indolo[3,2,1-jk]carbazolyl group has a small difference between the energy of a lowest excited triplet excited state (T1) and the energy of a lowest excited singlet excited state (S1).

An indolo[3,2,1-jk]carbazole compound according to an embodiment of the present invention having the indolo[3,2,1-jk]carbazolyl group therefore also has a small difference between the T1 energy and the S1 energy. Thus, the compound used in phosphorescent devices is expected to have a low driving voltage.

The indolo[3,2,1-jk]carbazolyl group in an indolo[3,2,1-jk]carbazole compound according to an embodiment of the present invention has a relatively deep HOMO level among nitrogen-containing heterocycles.

The phrase "deep HOMO level", as used herein, refers to a HOMO level spaced apart from the vacuum level. The phrase "shallow HOMO level", as used herein, refers to a HOMO level close to the vacuum level.

However, a compound having a plurality of indolo[3,2,1-jk]carbazolyl groups has a shallower HOMO level than those having one indolo[3,2,1-jk]carbazolyl group. Like an indolo[3,2,1-jk]carbazole compound according to an embodiment of the present invention, a compound having one indolo[3,2,1-jk]carbazolyl group has a HOMO level deeper than 6.0 eV. An indolo[3,2,1-jk]carbazole compound according to an embodiment of the present invention has a deep HOMO level and is consequently resistant to oxidation.

A compound having an indolo[3,2,1-jk]carbazolyl group not only has a deep HOMO level, but also is resistant to degradation caused by holes. Thus, a hole-blocking layer formed of an indolo[3,2,1-jk]carbazole compound according to an embodiment of the present invention is resistant to degradation caused by holes leaking from a light-emitting layer.

An indolo[3,2,1-jk]carbazole compound according to an embodiment of the present invention in which Ar in the general formula [1] is selected from aryl groups having a high T1 energy has a higher T1 energy than green phosphorescent materials. More specifically, the indolo[3,2,1-jk]carbazole compound has an energy of 490 nm or more. The green region is a region in the range of 500 to 530 nm.

Thus, an indolo[3,2,1-jk]carbazole compound according to an embodiment of the present invention can be used as a host material of a light-emitting layer in a green phosphorescent device.

An indolo[3,2,1-jk]carbazole compound according to an embodiment of the present invention, which has a deep HOMO level, can be used in a hole-blocking layer.

A host material is a compound that has the highest weight percentage among the compounds composing a light-emitting layer. A guest material is a compound that has a lower weight percentage than the host material and that is a principal light source. An assist material is a compound that has a lower weight percentage than the host material and that assists the guest material to emit light.

A hole-blocking layer is an organic compound layer adjacent to a cathode side of a light-emitting layer of an organic light-emitting device.

Indolo[3,2,1-jk]carbazole Compound According to an Embodiment of the Present Invention Specific structural formulae of an indolo[3,2,1-jk]carbazole compound according to an embodiment of the present invention will be described below.

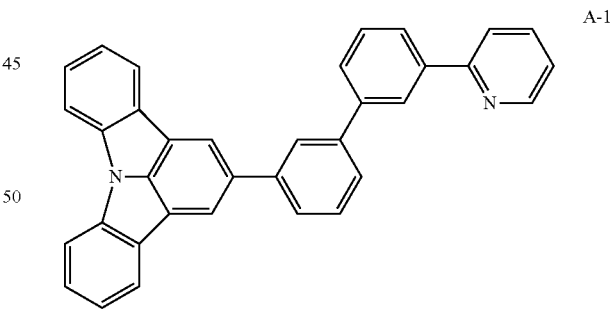

A-1

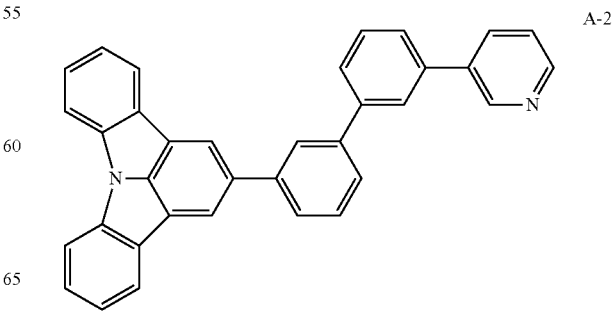

A-2

A-3
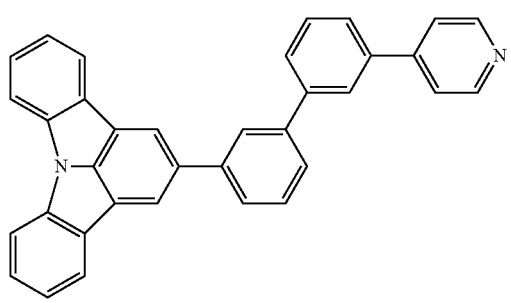
B-1
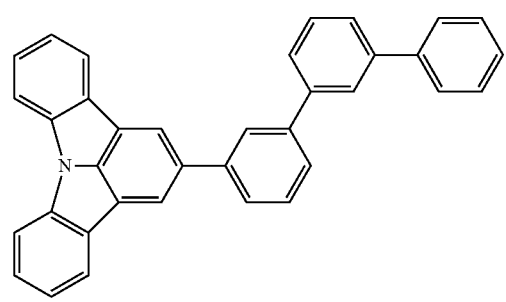
B-2
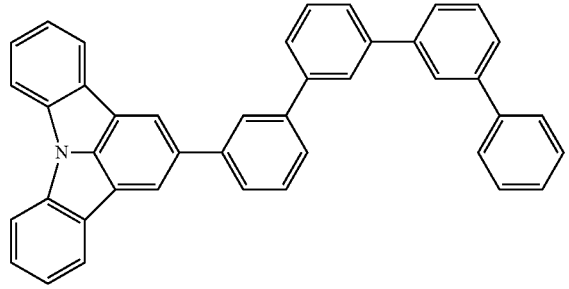
B-3
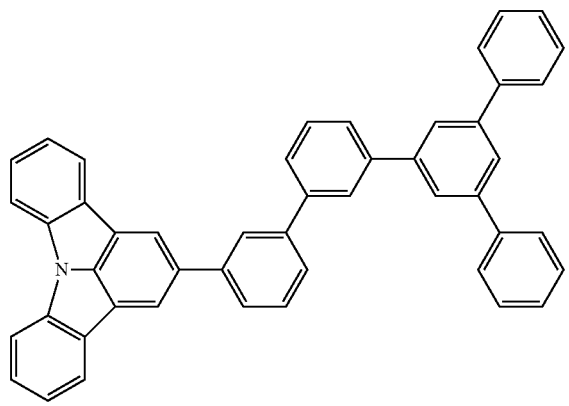
B-4
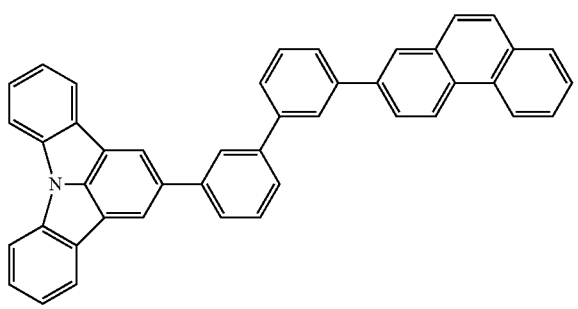
B-5
B-6
B-7
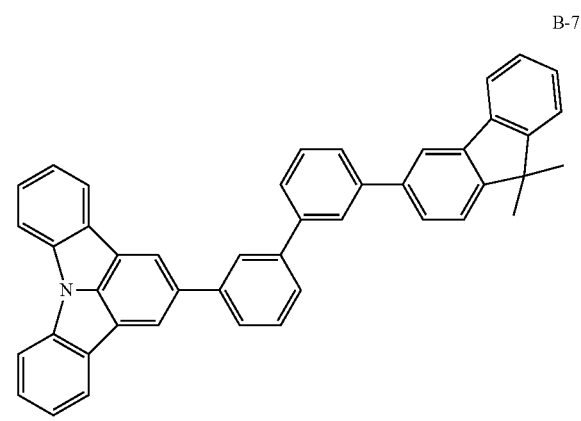

-continued

B-8
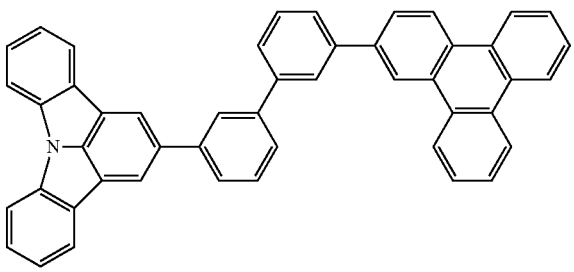

C-1
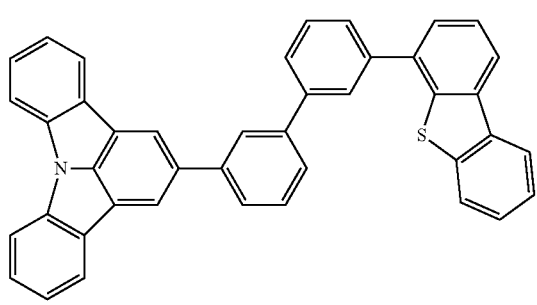

C-2
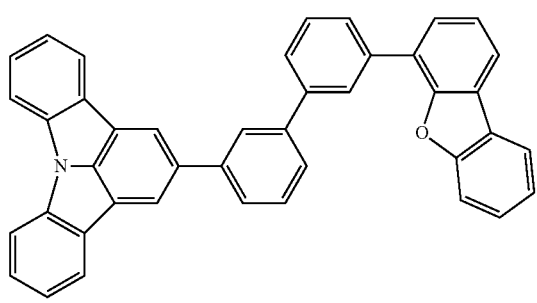

C-3
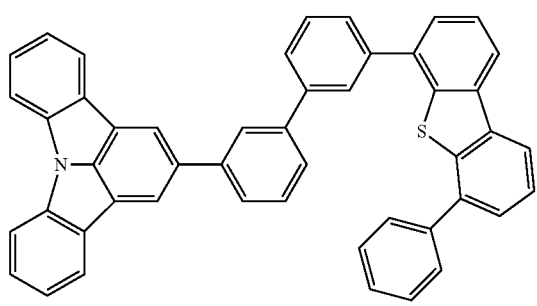

C-4
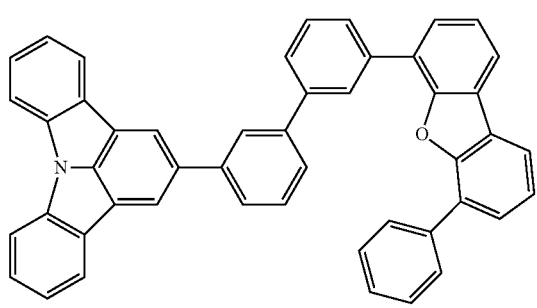

In the compound group A, Ar in the general formula [1] is a pyridyl group. The compounds of the group A are composed of a hydrogen atom, sp² carbon, and nitrogen.

Thus, the compounds of the group A have high chemical stability. An organic light-emitting device that contains a compound of the group A as a host material of a light-emitting layer is expected to have an extended life. Furthermore, the pyridyl group of Ar in the general formula [1] can improve electron conductivity of the molecule, providing a bipolar compound. Thus, a device that contains a compound of the group A can be driven at a low voltage.

The improved electron conductivity can increase the electron mobility of a light-emitting layer. Furthermore, the compounds of the group A can be used in a hole-blocking layer so as to increase the number of electrons injected into a light-emitting layer. This is because the hole-blocking layer does not inhibit the electron injection.

In the compound group B, Ar in the general formula [1] is a phenyl group, a biphenyl group, a terphenyl group, a phenanthryl group, a dimethylfluorenyl group, or a triphenylenyl group. The compounds of the group B are mainly composed of a hydrogen atom and sp² carbon.

Thus, the compounds of the group B have high chemical stability. An organic light-emitting device that contains a compound of the group B as a host material of a light-emitting layer is expected to have an extended life.

In the compound group C, Ar in the general formula [1] is a dibenzothienyl group or a dibenzofuranyl group. The compounds of the group C are composed of a hydrogen atom, sp² carbon, and sulfur or oxygen. Thus, the compounds of the group C have high chemical stability. An organic light-emitting device that contains a compound of the group A as a host material of a light-emitting layer is expected to have an extended life. The dibenzothienyl group of Ar in the general formula [1] can increase hole mobility and reduce electron mobility of the molecule. Thus, the compounds of the group C can be used to increase hole mobility of a light-emitting layer. Even when the dibenzothienyl group is introduced, the whole molecule has a deep HOMO level, and the electron mobility is low. This can reduce the number of electrons injected into a light-emitting layer. Thus, compounds having dibenzothienyl group can be used in a hole-blocking layer.

Since the dibenzothienyl group or the dibenzofuranyl group are reactive at positions 4 and 6, when the position 4 is bonded to a biphenyl group, the position 6 can be substituted with an aryl group, such as a phenyl group, to improve the stability of the compound.

Method for Synthesizing Indolo[3,2,1-jk]carbazole Compound According to an Embodiment of the Present Invention A method for synthesizing an indolo[3,2,1-jk]carbazole compound having the formula [1] according to the present embodiment will be described below.

As shown in the following formula [3], an indolo[3,2,1-jk] carbazole compound according to the present embodiment can be synthesized by coupling a boronic acid compound having Ar with 3,3'-dihalogen biphenyl in the presence of a Pd catalyst, followed by coupling with a bis(pinacolato)diboron ester compound of an indolo[3,2,1-jk]carbazole in the presence of a Pd catalyst. Alternatively, the 3,3'-dihalogen biphenyl may be first coupled with the bis(pinacolato)diboron ester compound of an indolo[3,2,1-jk]carbazole.

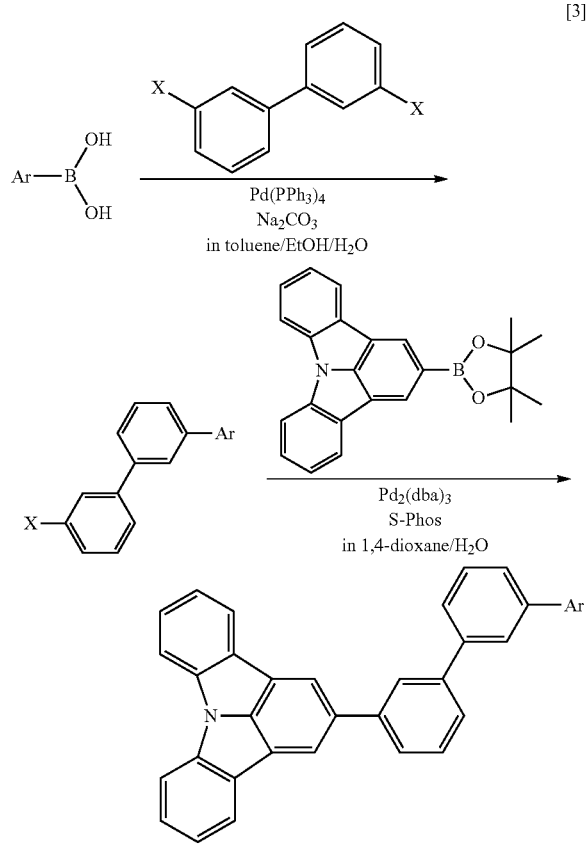

[3]

In the formula [3], Ar is selected from the aryl groups listed in the formula [2]. X denotes chlorine, bromine, or iodine.

In the reaction described above, an indolo[3,2,1-jk]carbazole compound can be synthesized by selecting appropriate Ar.

According to one aspect, an indolo[3,2,1-jk]carbazole compound according to an embodiment of the present invention for use in organic light-emitting devices may be purified by sublimation immediately before use. This is because organic compounds can be effectively purified by sublimation. In sublimation purification, an organic compound having a higher molecular weight generally requires a higher temperature. A high temperature tends to cause the thermal decomposition of the compound. Thus, in order to perform sublimation purification without excessive heating, an organic compound for use in organic light-emitting devices may have a molecular weight of 1000 or less.

Organic Light-Emitting Device According to the Present Embodiment

An organic light-emitting device according to the present embodiment includes a pair of electrodes, an anode and a cathode, and an organic compound layer between the electrodes. A layer containing a light-emitting material in the organic compound layer is a light-emitting layer. In the organic light-emitting device according to the present embodiment, the organic compound layer contains an indolo[3,2,1-jk]carbazole compound having the general formula [1].

An organic compound layer of an organic light-emitting device according to an embodiment of the present invention may be a monolayer or multilayer. The multilayer may be composed of layers selected from a hole-injection layer, a hole-transport layer, a light-emitting layer, a hole-blocking layer, an electron-transport layer, an electron-injection layer, and an exciton-blocking layer. As a matter of course, these layers may be used in combination.

The structure of an organic light-emitting device according to the present embodiment is not limited to those described above. For example, an insulating layer, an adhesive layer, or an interference layer may be disposed at an interface between an electrode and an organic compound layer. An electron-transport layer or a hole-transport layer may be formed of two sublayers having different ionization potentials.

The light-emitting device may be of a top emission type, a bottom emission type, or a top and bottom emission type. In the top emission type, light is extracted through an electrode adjacent to a substrate. In the bottom emission type, light is extracted through the surface spaced away from the substrate. In the top and bottom emission type, light is extracted through both surfaces.

An indolo[3,2,1-jk]carbazole compound according to an embodiment of the present invention may be used in any layer of the light-emitting device. For example, an indolo[3,2,1-jk]carbazole compound according to an embodiment of the present invention may be used as a host material of a light-emitting layer or a material of a hole-blocking layer.

The concentration of a host material in a light-emitting layer is 50% by weight or more and 99.9% by weight or less, such as 80% by weight or more and 99.9% by weight or less, of the total weight of the light-emitting layer. The concentration of a guest material may be 10% by weight or less to prevent concentration quenching.

A guest material may be distributed uniformly or with a concentration gradient in a layer made of a host material. Alternatively, the host material layer may include a region containing a guest material and a region free of the guest material.

The light-emitting material of an organic light-emitting device according to the present embodiment may be a green phosphorescent material. Alternatively, the light-emitting material may be a blue light-emitting material having a peak wavelength of 450 nm or more and 470 nm or less.

In a phosphorescent organic light-emitting device, in order to prevent a reduction in luminous efficiency due to nonradiative deactivation from T1 of a host material, the T1 energy of the host material may be higher than the T1 energy of a guest material, that is, a phosphorescent material.

An indolo[3,2,1-jk]carbazole compound according to an embodiment of the present invention has a deep HOMO level and a high T1 energy and can therefore be used as a hole-blocking material.

In a green or blue phosphorescent device, sublayers of an organic compound layer have a large energy gap therebetween. Thus, a light-emitting layer tends to have a deep HOMO level. A host material, such as 4,4'-biscarbazolyl-1,1'-biphenyl (CBP) or 3,3'-biscarbazolyl-1,1'-biphenyl (mCBP), has a HOMO level in the range of approximately 5.8 to 5.9 eV. A hole-blocking layer can function well when a difference in HOMO level between the light-emitting layer and the hole-blocking layer is 0.1 eV or more.

According to one aspect, a hole-blocking material for use in a phosphorescent device may have a HOMO level as deep as possible, such as more than 6.0 eV.

Use of such a hole-blocking material can increase the life of the device. This is because even if a change in carrier balance causes holes in a light-emitting layer to leak from a hole-blocking layer, an amine in the hole-blocking layer can prevent the degradation of the hole-blocking layer.

In the case that an indolo[3,2,1-jk]carbazole compound according to an embodiment of the present invention is used as a host material of a light-emitting layer or a material of a hole-blocking layer, a phosphorescent material to be used as a guest material of the light-emitting layer may be a metal complex, such as an iridium complex, a platinum complex, a rhenium complex, a copper complex, an europium complex, or a ruthenium complex. An iridium complex can emit strong phosphorescence. The light-emitting layer may also contain a plurality of phosphorescent materials to facilitate exciton or carrier transportability.

In addition to a compound according to an embodiment of the present invention, conventionally known low-molecular-weight and high-molecular-weight compounds may optionally be used. More specifically, a compound according to an embodiment of the present invention may be used in combination with a hole-injection or hole-transport compound, a host material, a light-emitting compound, an electron-injection compound, or an electron-transport compound.

Examples of these compounds will be described below.

The hole-injection or hole-transport compound may facilitate the injection of holes from an anode and have high hole mobility to transport the injected holes to a light-emitting layer. Examples of low-molecular-weight and high-molecular-weight hole-injection or hole-transport compounds include, but are not limited to, triarylamine derivatives, phenylenediamine derivatives, stilbene derivatives, phthalocyanine derivatives, porphyrin derivatives, polyvinylcarbazole, polythiophene, and other electroconductive polymers.

Examples of light-emitting materials include, but are not limited to, phosphorescent guest materials described above and derivatives thereof, fused-ring compounds (for example, fluorene derivatives, naphthalene derivatives, pyrene derivatives, perylene derivatives, tetracene derivatives, anthracene derivatives, and rubrene), quinacridone derivatives, coumarin derivatives, stilbene derivatives, organoaluminum complexes, such as tris(8-quinolinolato)aluminum, organic beryllium complexes, and polymer derivatives, such as polyphenylenevinylene derivatives, polyfluorene derivatives, and polyphenylene derivatives.

The electron-injection or electron-transport compound may facilitate the injection of electrons from a cathode and can transport the injected electron to a light-emitting layer. The electron-injection or electron-transport compound is selected in consideration of the hole mobility of the hole-injection or hole-transport compound. Examples of the electron-injection or electron-transport compound include, but are not limited to, oxadiazole derivatives, oxazole derivatives, pyrazine derivatives, triazole derivatives, triazine derivatives, quinoline derivatives, quinoxaline derivatives, phenanthroline derivatives, and organoaluminum complexes.

According to one aspect, the material for an anode may have a work function as high as possible. Examples of the anode material include, but are not limited to, metallic elements, such as gold, platinum, silver, copper, nickel, palladium, cobalt, selenium, vanadium, and tungsten, alloys of these metallic elements, and metal oxides, such as tin oxide, zinc oxide, indium oxide, indium tin oxide (ITO), and indium zinc oxide. Examples of the anode material also include, but are not limited to, electroconductive polymers, such as polyaniline, polypyrrole, and polythiophene. These anode materials may be used alone or in combination. An anode may be a monolayer or multilayer.

According to one aspect, the material for a cathode may have a work function as low as possible. Examples of the cathode material include, but are not limited to, alkali metals, such as lithium, alkaline-earth metals, such as calcium, metallic elements, such as aluminum, titanium, manganese, silver, lead, and chromium, and alloys of the metallic elements. Metal oxides, such as indium tin oxide (ITO), may also be used. These cathode materials may be used alone or in combination. The cathode may be a monolayer or multilayer.

An organic compound layer of an organic light-emitting device according to the present embodiment can be formed as described below. In general, a thin film is formed by vacuum evaporation, ionized deposition, sputtering, plasma chemical vapor deposition (CVD), or a known coating method (for example, spin coating, dipping, casting, a Langmuir-Blodgett (LB) method, or an ink jet method) using a solution in an appropriate solvent.

A layer formed by vacuum evaporation or solution coating experiences little crystallization and has excellent temporal stability. Using a coating method, a film can be formed using an appropriate binder resin.

Examples of the binder resin include, but are not limited to, polyvinylcarbazole resins, polycarbonate resins, polyester resins, ABS resins, acrylic resins, polyimide resins, phenolic resins, epoxy resins, silicone resins, and urea resins. These binder resins may be used alone as a homopolymer or a copolymer or may be used in combination. Optionally, a known additive agent, such as a plasticizer, an antioxidant, and/or an ultraviolet absorber, may be used.

Applications of Organic Light-Emitting Device

An organic light-emitting device according to an embodiment of the present invention can be used in display apparatuses and lighting apparatuses. An organic light-emitting device according to an embodiment of the present invention can also be used in exposure light sources of electrophotographic image-forming apparatuses and backlights of liquid crystal displays.

A display apparatus includes an organic light-emitting device according to the present embodiment in a display. The display includes a plurality of pixels. Each of the pixels includes an organic light-emitting device according to the present embodiment and a TFT device, which is one of switching devices for controlling luminance. An anode or a cathode of the organic light-emitting device is connected to a drain electrode or a source electrode of the TFT device. The display apparatus can be used as an image display apparatus in personal computers (PCs).

The display apparatus may be an image input apparatus that includes an input unit. Image information from an area charge-coupled device (CCD), a linear CCD, a memory card, or the like is input to the input unit. The image is then output to a display. The display apparatus may have an image output function as a display for use in image pickup apparatuses or ink jet printers and an input function as an operation panel. Using the image output function, the display apparatus can display image information from the outside. Using the input function, information on image processing can be input. The display apparatus may be used as a display for multifunction printers.

A display apparatus that includes an organic light-emitting device according to the present embodiment will be described below with reference to the FIGURE.

The FIGURE is a schematic cross-sectional view of a display apparatus that includes an organic light-emitting device according to the present embodiment and a TFT device connected to the organic light-emitting device. The TFT device is a switching device. The FIGURE illustrates two sets of the organic light-emitting device and the TFT device. This structure will be described in detail below.

The display apparatus includes a substrate 1, for example, made of glass, a moisture-proof film 2 for protecting a TFT device or an organic compound layer, a metal gate electrode 3, a gate-insulating film 4, and a semiconductor layer 5.

Each of TFT devices 8 includes a semiconductor layer 5, a drain electrode 6, and a source electrode 7. The TFT devices 8 are covered with an insulating film 9. Each anode 11 of the organic light-emitting devices is connected to a source electrode 7 through a contact hole 10. The display apparatus may have any structure provided that the anode or the cathode of each of the organic light-emitting devices is connected to the source electrode or the drain electrode of the corresponding TFT device.

A multilayer organic compound layer 12 is illustrated as a single layer in the FIGURE. Cathodes 13 are covered with a first protective layer 14 and a second protective layer 15 for preventing degradation of the organic light-emitting devices.

In the display apparatus according to the present embodiment, the switching device is not particularly limited and may be a single-crystal silicon substrate, a MIM device, or an a-Si device.

EXAMPLES

Example 1

Synthesis of Exemplary Compound C-1

(1) Synthesis of Intermediate PCz-PB

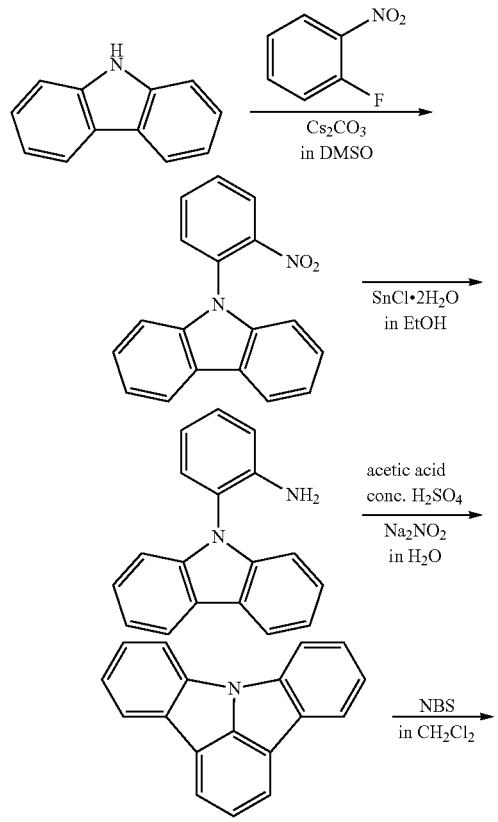

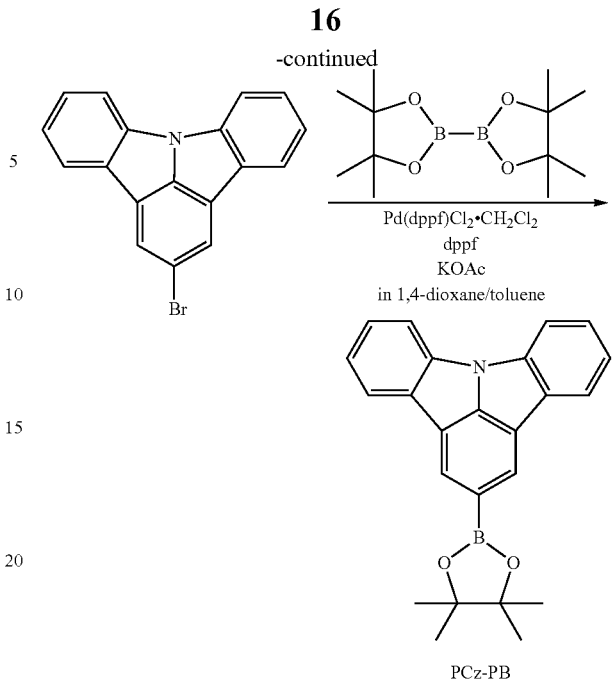

The following reagents and solvents were charged into a reactor.
9H-carbazole: 120 g (0.718 mol)
2-fluoronitrobenzene: 106 g (0.754 mol)
Cesium carbonate: 152 g (1.077 mol)
Dehydrated dimethyl sulfoxide: 1.8 L This reaction solution was stirred under nitrogen at room temperature for three days. After the completion of the reaction, the reaction solution was poured into 3 L of ice water. Precipitated yellow solid was stirred at room temperature for 30 minutes and was filtered. The filtered solid was dissolved in 3 L of chloroform, was washed with water, was dried over magnesium sulfate, and was concentrated to yield 229 g of a yellow solid 9-(2-nitrophenyl)-9H-carbazole.

Subsequently, the following reagents and solvents were charged into a reactor.
9-(2-nitrophenyl)-9H-carbazole: 229 g (0.794 mol)
$SnCl_2.2H_2O$: 567 g (2.51 mol)
Ethanol: 5 L This reaction solution was stirred under nitrogen at an internal temperature of 70° C. for eight hours. After the completion of the reaction, the reaction solution was cooled and concentrated. Five liters of 1 N aqueous sodium hydroxide was added to the residue. The suspension was stirred at room temperature for one hour and was filtered. The filtered solid was dissolved in 8 L of toluene. Seven liters of 1 N aqueous sodium hydroxide was added to the toluene solution. After separation, an aqueous layer was extracted, and an organic layer was washed with water. The organic layer was then dried over magnesium sulfate, was concentrated once, and was heated and washed in suspension with isopropyl ether to yield 124 g of a pale yellow solid 2-(9H-carbazole-9-yl)aniline (yield 61%).

Subsequently, the following reagents and solvents were charged into a reactor.
2-(9H-carbazole-9-yl)aniline: 124 g (0.480 mol)
Acetic acid: 1.2 L
Concentrated sulfuric acid: 124 ml This reaction solution was cooled to an internal temperature of 10° C. in an ice-water bath. 33.8 g of sodium nitrite in 670 ml of distilled water was added dropwise for 15 minutes. After agitation for 10 minutes, the reaction solution was stirred at an external temperature of 130° C. for 20 minutes.

After the completion of the reaction, the reaction solution was cooled. One liter of distilled water was added to the reaction solution. A precipitated solid was filtered out. The resulting yellowish brown solid was washed in suspension with 2 L of methanol to yield a brown solid. This solid was purified by column chromatography (silica gel) and was recrystallized in a mixed solvent of chloroform and ethanol, yielding 83.3 g of an orange-white solid indolo[3,2,1-jk]carbazole (yield 72%).

Subsequently, the following reagents and solvents were charged into a reactor while being shaded from the light.
Indolo[3,2,1-jk]carbazole: 83.3 g (0.345 mol)
N-bromosuccinimide: 67.6 g
Dehydrated methylene chloride: 3.3 L This reaction solution was stirred at room temperature for one hour while still being shaded from the light. 250 g of silica gel was added to the reaction solution. The reaction solution was stirred at room temperature for 13 hours. After the completion of the reaction, the silica gel was removed. The silica gel was washed three times with 1 L of chloroform in total. The chloroform was collected, washed with water, dried over anhydrous sodium sulfate, and concentrated. The concentrated solid was recrystallized in toluene and was heated and washed with acetic acid to yield 62.2 g of a white solid 2-bromoindolo[3,2,1-jk]carbazole (yield 57%).

The compound was identified by $^1$H-NMR analysis.
$^1$H-NMR (300 MHz, CDCl$_3$)
δ 8.12 (s, 2H), 8.06-8.03 (d, 2H), 7.87-7.84 (d, 2H), 7.59-7.53 (t, 2H), 7.38-7.32 (t, 2H)

Subsequently, the following reagents and solvents were charged into a reactor while being shaded from the light.
2-bromoindolo[3,2,1-jk]carbazole: 55.0 g (0.172 mol)
Bis(pinacolato)diboron: 52.4 g (0.206 mol)
[1,1'-bis(diphenylphosphino)ferrocene]palladium(II) dichloride dichloromethane adduct: 2.11 g (2.58 mmol)
1,1'-bis(diphenylphosphino)ferrocene: 1.43 g (2.58 mmol)
Potassium acetate: 42.2 g (0.430 mol)
Dehydrated 1,4-dioxane: 550 ml
Dehydrated toluene: 550 ml This reaction solution was degassed and was stirred under argon at an external temperature of 120° C. for 17 hours. After the completion of the reaction, the reaction solution was cooled and concentrated. The concentrated solid was heated and washed in suspension with toluene and was purified by column chromatography (silica gel) to yield a white solid. This solid was washed with hexane and isopropyl ether to yield 48 g of a white solid PCz-PB (yield 76%).

The compound was identified by $^1$H-NMR analysis.
$^1$H-NMR (300 MHz, CDCl$_3$)
δ 8.57 (s, 2H), 8.15-8.13 (d, 2H), 7.93-7.90 (d, 2H), 7.59-7.53 (t, 2H), 7.39-7.34 (t, 2H), 1.45 (s, 12H)

(2) Synthesis of Exemplary Compound C-1

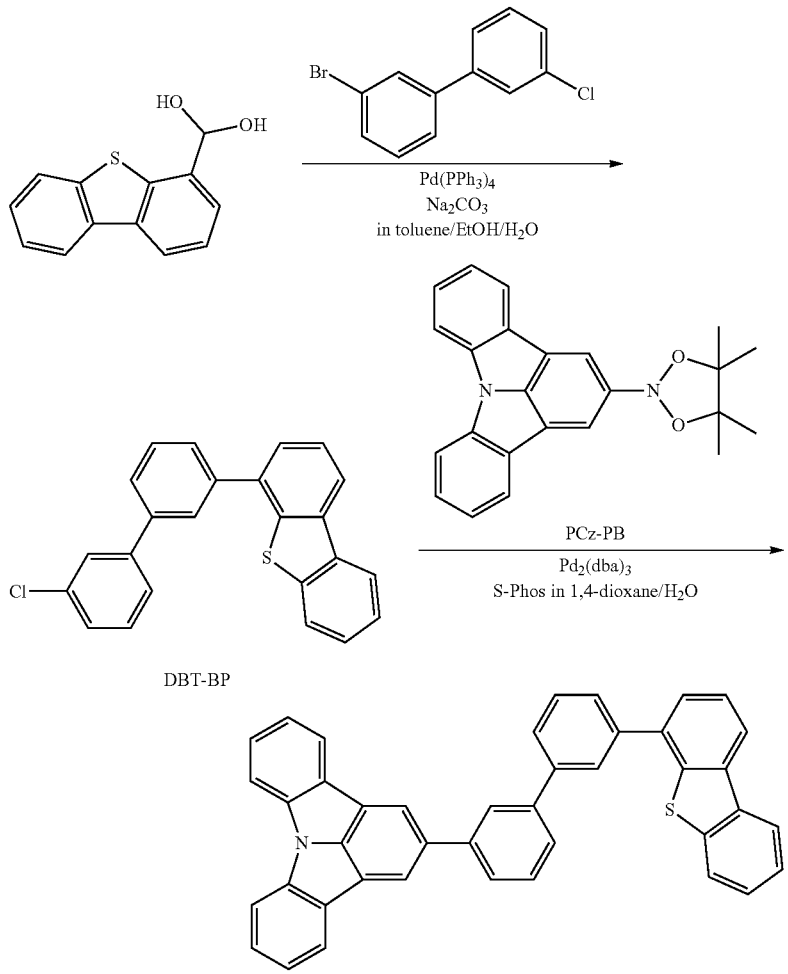

C-1

The following reagents and solvents were charged into a reactor.

4-dibenzothiopheneboronic acid: 1.88 g (8.22 mmol)
3-bromo-3'-chlorobiphenyl: 2.0 g (7.48 mmol)
Tetrakis(triphenylphosphine)palladium(0): 432 mg (0.374 mmol)
Toluene: 120 mL
Ethanol: 60 mL
30% by weight cesium carbonate aqueous solution: 60 mL This reaction solution was degassed and was stirred under nitrogen at an external temperature of 80° C. for 7 hours. After the completion of the reaction, the reaction solution was cooled. 200 ml of water was added to the reaction solution. After separation, an aqueous layer was extracted, and an organic layer was washed with water and was purified by column chromatography (silica gel) to yield 2.28 g of a white solid DBT-BP (yield 82%).

Subsequently, the following reagents and solvents were charged into a reactor.

PCz-PB: 1.0 g (2.72 mmol)
DBT-BP: 0.92 g (2.48 mmol)
Tris(dibenzylideneacetone)dipalladium(0): 91 mg (0.099 mmol)
2-dicyclohexylphosphino-2',6'-dimethoxybiphenyl: 94 mg (0.198 mmol)
Tripotassium phosphate: 2.10 g (9.90 mmol)
Toluene: 100 ml
Water: 0.1 ml This reaction solution was degassed and was stirred under nitrogen at an external temperature of 135° C. for 7 hours. After the completion of the reaction, the reaction solution was cooled. 200 ml of water was added to the reaction solution. After separation, an aqueous layer was extracted, and an organic layer was washed with water and was concentrated. The concentrated crude product was heated and dissolved in chlorobenzene. The resulting hot solution was filtered with silica gel and was concentrated again. The concentrated solid was heated and washed in suspension with ethanol to yield a white solid. The white solid was recrystallized three times in a mixed solvent of chlorobenzene and ethanol to yield 1.09 g of a white solid C-1 (yield 76%). The resulting crystal was then dried under vacuum at 130° C. and was subjected to sublimation purification at $10^{-4}$ Pa at 340° C., yielding 850 mg of a high-purity exemplary compound C-1.

The exemplary compound C-1 was identified as described below.

MALDI-TOF-MS
Actual value: m/z=575.21
Calculated value: $C_{42}H_{25}NS$=575.72
[$^1$H-NMR (400 MHz, $CDCl_3$)]
δ 8.31 (s, 2H), 8.21-8.16 (m, 4H), 8.12 (s, 1H), 8.07 (s, 1H), 7.93-7.91 (d, 2H), 7.85-7.75 (m, 4H), 7.73-7.70 (d, 1H), 7.66-7.62 (m, 2H), 7.60-7.55 (m, 4H), 7.50-7.43 (m, 2H), 7.39-7.35 (t, 2H)

The T1 energy of the exemplary compound C-1 was measured as described below.

The phosphorescence spectrum of a dilute solution of the exemplary compound C-1 in toluene was measured in an argon atmosphere at 77 K at an excitation wavelength of 350 nm. The T1 energy determined from the first peak wavelength of the phosphorescence spectrum corresponded to a wavelength of 440 nm.

The exemplary compound C-1 was then heated and deposited on a glass substrate to form a thin film having a thickness of 20 nm. The phosphorescence spectrum of the thin film was measured in an argon atmosphere at 77 K at an excitation wavelength of 350 nm. The T1 energy determined from the first peak wavelength of the phosphorescence spectrum corresponded to a wavelength of 480 nm.

The ionization potential of the exemplary compound C-1 was measured as described below.

The ionization potential of the evaporated thin film used in the measurement of the energy gap described above was measured with a photoelectron spectrometer AC-3 (manufactured by Riken Keiki Co., Ltd.). The ionization potential of the exemplary compound C-1 was 6.01 eV.

The solubility of the exemplary compound C-1 was measured as described below.

The amount of chlorobenzene required to dissolve 10 mg of the exemplary compound C-1 was determined. As a result, the amount of chlorobenzene required to dissolve 10 mg of the exemplary compound C-1 was 1 ml or less.

This proved that the compound according to the present example had a high solubility. When used in an organic light-emitting device, a compound having a high solubility is prevented from being crystallized.

Example 2

Synthesis of Exemplary Compound B-3

790 mg of a white solid exemplary compound B-3 was synthesized in the same manner as in Example 1 except that dibenzothiopheneboronic acid in (2) was replaced with 2-([1,1':3',1''-terphenyl]-5'-yl)-4,4,5,5-tetramethyl-1,3,2-dioxaborolane.

The phosphorescence spectrum of a dilute solution of the exemplary compound B-3 in toluene was measured in an argon atmosphere at 77 K at an excitation wavelength of 350 nm. The T1 energy determined from the first peak wavelength of the phosphorescence spectrum corresponded to a wavelength of 440 nm.

The ionization potential of the exemplary compound B-3 was measured as described below.

The ionization potential of the evaporated thin film used in the measurement of the energy gap described above was measured with a photoelectron spectrometer AC-3 (manufactured by Riken Keiki Co., Ltd.). The ionization potential of the exemplary compound B-3 was 6.03 eV.

The solubility of the exemplary compound B-3 was measured as described below.

The amount of chlorobenzene required to dissolve 10 mg of the exemplary compound B-3 was determined. As a result, the amount of chlorobenzene required to dissolve 10 mg of the exemplary compound B-3 was 2 ml.

Example 3

Synthesis of Exemplary Compound A-2

330 mg of a white solid exemplary compound A-2 was synthesized in the same manner as in Example 1 except that dibenzothiopheneboronic acid in (2) was replaced with 3-pyridylboronic acid.

The phosphorescence spectrum of a dilute solution of the exemplary compound A-2 in toluene was measured in an argon atmosphere at 77 K at an excitation wavelength of 350 nm. The T1 energy determined from the first peak wavelength of the phosphorescence spectrum corresponded to a wavelength of 440 nm.

The ionization potential of the exemplary compound A-2 was measured as described below.

The ionization potential of the evaporated thin film used in the measurement of the energy gap described above was measured with a photoelectron spectrometer AC-3 (manufactured by Riken Keiki Co., Ltd.). The ionization potential of the exemplary compound A-2 was 6.12 eV.

The solubility of the exemplary compound A-2 was measured as described below.

The amount of chlorobenzene required to dissolve 10 mg of the exemplary compound A-2 was determined. As a result, the amount of chlorobenzene required to dissolve 10 mg of the exemplary compound A-2 was 1 ml.

Comparative Example 1

Comparisons of Ionization Potential and Solubility

The ionization potential and the solubility of the following comparative compounds FH-01 and FH-02 were measured in the same way as in Example 1. Table 1 shows the results for FH-01 and FH-02, together with the results for Examples 1 to 3.

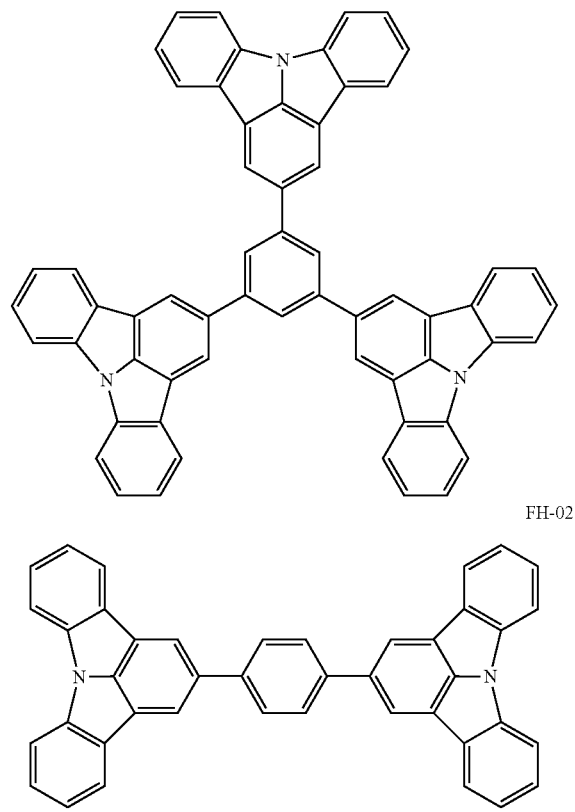

TABLE 1

|  | Ionization potential (eV) | Color of film 2 h after film formation | Amount of chlorobenzene required to dissolve 10 mg of compound (ml) |
| --- | --- | --- | --- |
| Exemplary compound C-1 | 6.01 | Clear | 1 |
| Exemplary compound B-3 | 6.03 | Clear | 2 |
| Exemplary compound A-2 | 6.12 | Clear | 1 |
| Comparative compound FH-01 | 5.83 | Pale yellowish brown | 50 or more |
| Comparative compound FH-02 | 5.72 | Pale yellowish brown | 10 |

The HOMO levels of the comparative compounds FH-01 and FH-02, which had a plurality of indolo[3,2,1-jk]carbazolyl groups, were lower than those of Examples 1 to 3 by 0.2 eV or more.

The comparative compounds FH-01 and FH-02 had 10 times or more lower solubility than the exemplary compound C-1. In particular, the comparative compound FH-01 had 50 times or more lower solubility than the exemplary compound C-1. This indicates that the comparative compounds FH-01 and FH-02 had a high degree of crystallinity.

The evaporated films of the comparative compounds FH-01 and FH-02 on a glass substrate changed in color to pale yellowish brown after being left to stand in the air at room temperature for approximately two hours. In contrast, the evaporated film of the exemplary compound C-1 did not change in color. This suggests that the evaporated films of the comparative compounds FH-01 and FH-02 were oxidized because of their shallow HOMO levels.

These results show that the indolo[3,2,1-jk]carbazole compounds according to the examples had an excellent membrane property, a high T1 energy, and a deep HOMO level.

Example 4

A bottom emission type organic light-emitting device was fabricated as described below. This device included an anode, a hole-transport layer, a light-emitting layer, a hole-blocking layer, an electron-transport layer, and a cathode on a substrate in this order.

An indium zinc oxide (IZO) film having a thickness of 120 nm was formed as the anode on the glass substrate by sputtering. This substrate was used as a transparent electroconductive supporting substrate (IZO substrate). An organic compound layer and an electrode layer were continuously formed on the IZO substrate in a vacuum chamber at $10^{-5}$ Pa by vacuum evaporation using resistance heating. The emission area was 3 mm$^2$.

Hole-transport layer (40 nm) HTL-1

Light-emitting layer (30 nm) Host material: C-1, Guest material: Ir-1 (10% by weight)

Hole-blocking layer (10 nm) HBL-1

Electron-transport layer (30 nm) ETL-1

Metal electrode layer 1 (0.5 nm) LiF

Metal electrode layer 2 (100 nm) Al

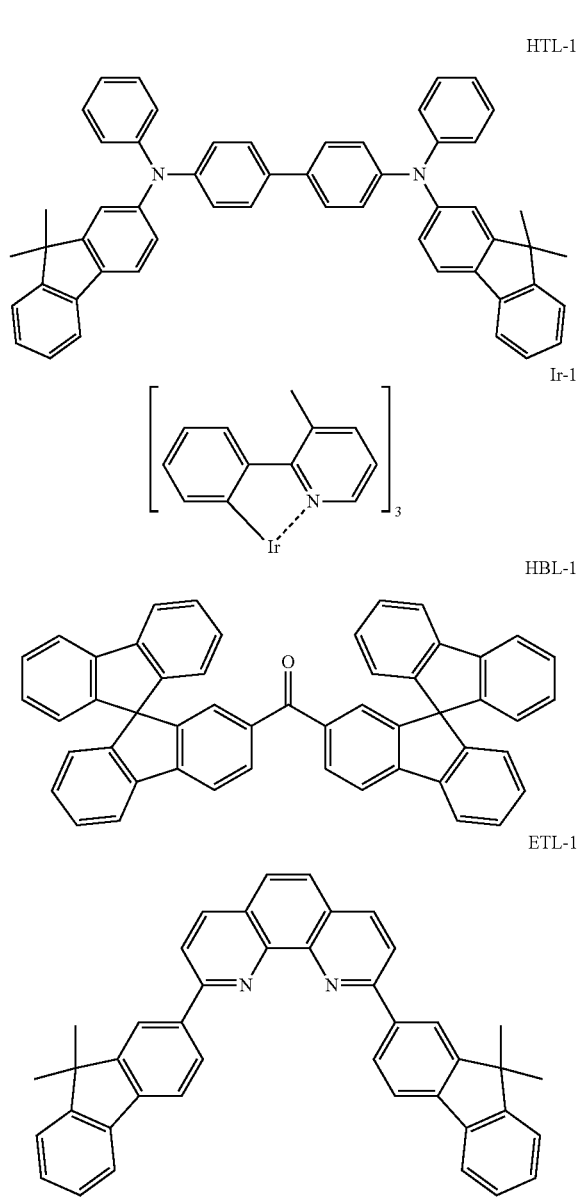

In order to prevent degradation caused by moisture adsorption, the organic light-emitting device was covered with a protective glass plate and was sealed with an acrylic resin binder in a dry air atmosphere. Through these processes, the organic light-emitting device was fabricated.

A voltage of 6.5 V was applied between a positive ITO electrode and a negative Al electrode of the organic light-emitting device. As a result, a green light emission was observed in which the luminous efficiency was 47 cd/A, and the CIE chromaticity coordinates were (x, y)=(0.35, 0.62). When a voltage was applied to the organic light-emitting device in a nitrogen atmosphere at an electric current density of 40 mA/cm$^2$, the luminance after 100 hours reached 0.75 times as the initial luminance. The current-voltage characteristics of the organic light-emitting device were measured with an ammeter 2700 manufactured by Keithley Instruments, Inc. The luminance of the organic light-emitting device was measured with BM7-fast manufactured by Topcon Corp.

HTL-1, Ir-1, HBL-1, and ETL-1 in Example 4 were synthesized with reference to WO 2009/139501, Optical and electroluminescent properties of a new green emitting Ir(III) complex. (Rupasree R. Das et al., Optical Materials, Vol. 21, p. 143 (2002)), WO 2004/093207, and WO 2009/139501, respectively.

Comparative Example 2

An organic light-emitting device was fabricated in the same manner as in Example 4 except that the host material, the exemplary compound C-1, was replaced with the comparative compound FH-02.

The organic light-emitting device was tested in the same manner as in Example 4. At an applied voltage of 7.4 V, a green light emission was observed with a luminous efficiency of 40 cd/A. When a voltage was applied to the organic light-emitting device in a nitrogen atmosphere at an electric current density of 40 mA/cm$^2$, the luminance after 50 hours reached 0.63 times as the initial luminance.

Example 5

A top emission type organic light-emitting device was fabricated.

An Al film was formed on a transparent glass substrate by sputtering. An indium zinc oxide (IZO) film having a thickness of 38 nm was formed as a transparent electrode on the Al film by sputtering. A pixel isolation film was then patterned with an acrylic resin to prepare a substrate having an electrode area of 3 mm$^2$. The following organic layers were formed on the IZO substrate in a vacuum chamber at 10$^{-5}$ Pa by vacuum evaporation using resistance heating. A transparent electrode layer was formed by sputtering.

A device thus fabricated was sealed in an inert atmosphere with a glass cap having a moisture absorbent.

Hole-transport layer (13 nm): HTL-1

Light-emitting layer (20 nm) Host material: U-1, Guest material 1: Ir-1 (weight ratio 10%), Guest material 2: HBL-1 (weight ratio 20%)

Hole-blocking layer: C-1

Electron-transport layer (10 nm): ETL-1

Electron-injection layer (20 nm): co-evaporation of ETL-1 and cesium carbonate (3% by weight)

Transparent electrode layer (30 nm): IZO

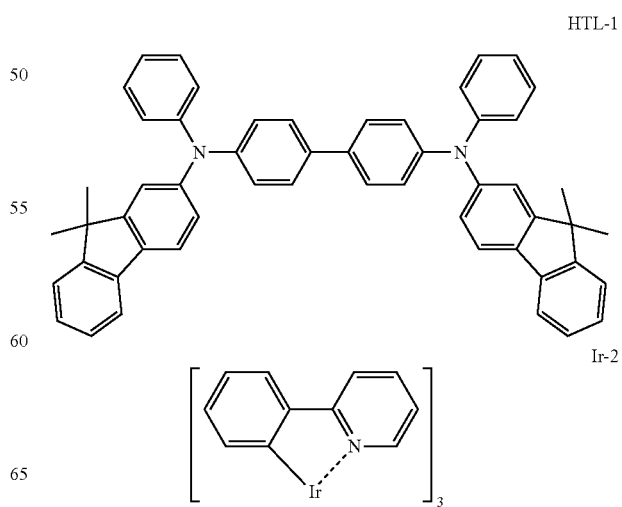

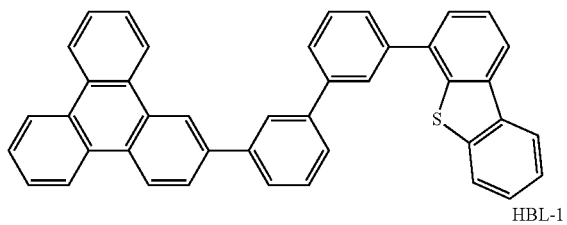
HBL-1

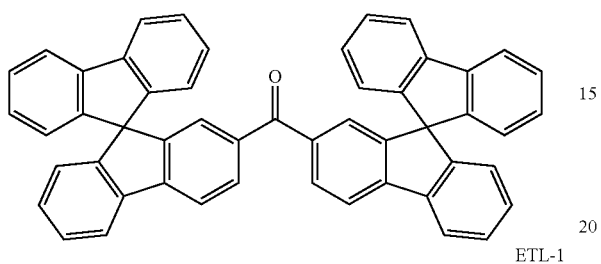
ETL-1

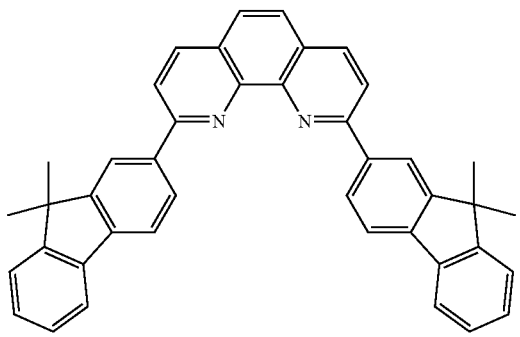

In the same manner as in Example 4, a voltage of 5.4 V was applied between a positive ITO electrode and a negative Al electrode of the organic light-emitting device. As a result, a green light emission was observed in which the luminous efficiency was 54 cd/A, and the CIE chromaticity coordinates were (x, y)=(0.24, 0.71). When a voltage was applied to the organic light-emitting device in a nitrogen atmosphere at an electric current density of 40 mA/cm$^2$, the luminance after 40 hours reached 0.90 times as the initial luminance.

HTL-1, Ir-2, HBL-1, U-1, and ETL-1 in Example 5 were synthesized with reference to WO 2009/139501, A New Synthetic Route to the Preparation of a Series of Strong Photoreducing Agents: fac Tris-Ortho-Metalated Complexes of Iridium(III) with Substituted 2-Phenylpyridines. (K. Dedeian et al., Inorganic Chemistry, Vol. 30, No. 8, p. 1685 (1991)), WO 2009/021126, WO 2004/093207, and WO 2009/139501, respectively.

Thus, an indolo[3,2,1-jk]carbazole compound according to aspects of the present invention is a novel compound having an excellent membrane property, a high T1 energy, and a deep HOMO level. An indolo[3,2,1-jk]carbazole compound according to aspects of the present invention can provide an organic light-emitting device having a low driving voltage, a high luminous efficiency, and high durability.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-219484 filed Sep. 29, 2010, which is hereby incorporated by reference herein in its entirety.

What is claimed is:

1. An indolo[3,2,1-jk]carbazole compound represented by the following general formula [1]:

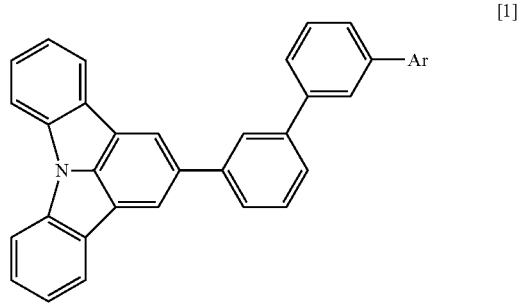

wherein Ar is selected from the substituents listed in the formula [2]

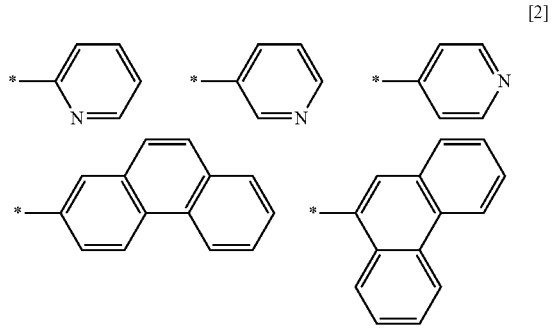
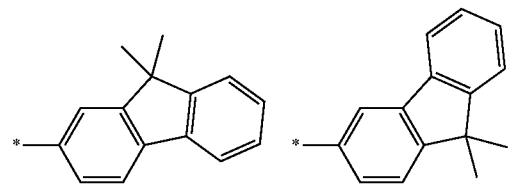
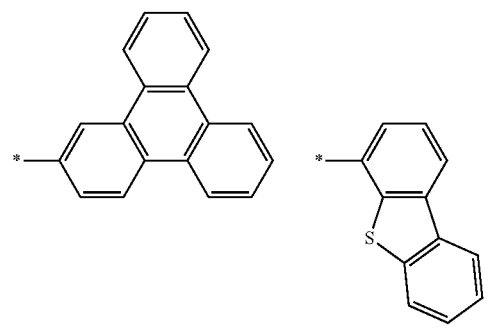

-continued

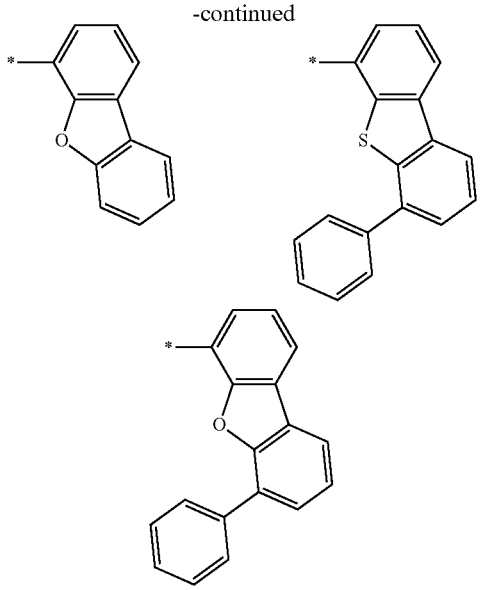

wherein * denotes a site to be bonded to the biphenyl group of the formula [1].

2. An organic light-emitting device, comprising:
a pair of electrodes; and
an organic compound layer between the pair of electrodes, wherein the organic compound layer contains an indolo[3,2,1-jk]carbazole compound according to claim 1.

3. The organic light-emitting device according to claim 2, wherein the organic compound layer is a light-emitting layer.

4. The organic light-emitting device according to claim 3, wherein the light-emitting layer contains a host material and a guest material, the host material is the indolo[3,2,1-jk]carbazole compound, and the guest material is a phosphorescent material.

5. The organic light-emitting device according to claim 4, wherein the phosphorescent material is an iridium complex.

6. The organic light-emitting device according to claim 2, wherein the pair of electrodes are an anode and a cathode, the organic compound layer is a hole-blocking layer, and the hole-blocking layer is in contact with a cathode side of a light-emitting layer.

7. A display apparatus comprising a plurality of pixels, wherein each of the pixels includes an organic light-emitting device according to claim 2 and a switching device connected to the organic light-emitting device.

8. An image input apparatus, comprising:
a display configured to display an image; and
an input unit to which image information is to be input, wherein the display includes a plurality of pixels, and each of the pixels includes an organic light-emitting device according to claim 2 and a switching device connected to the organic light-emitting device.

9. A display apparatus comprising a plurality of pixels, wherein each of the pixels includes an organic light-emitting device according to claim 6 and a switching device connected to the organic light-emitting device.

10. An image input apparatus, comprising:
a display configured to display an image; and
an input unit to which image information is to be input, wherein the display includes a plurality of pixels, and each of the pixels includes an organic light-emitting device according to claim 6 and a switching device connected to the organic light-emitting device.

11. A lighting apparatus comprising the organic light-emitting device according to claim 2.

12. An apparatus comprising a substrate and the organic light-emitting device according to claim 2.

13. A lighting apparatus comprising the organic light-emitting device according to claim 6.

14. An apparatus comprising a substrate and the organic light-emitting device according to claim 6.

15. The indolo[3,2,1-jk]carbazole compound according to claim 1,
wherein the Ar is selected from the substituents listed in the formula [3] below:

[3]

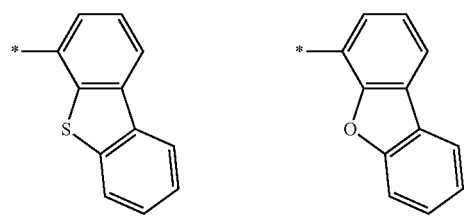

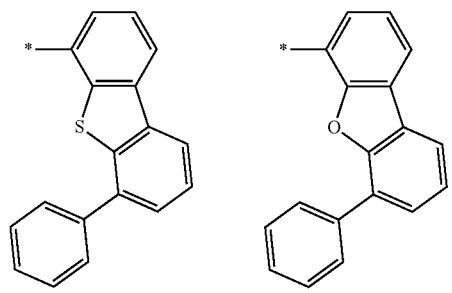

wherein * denotes a site to be bonded to the biphenyl group of the formula [1].

16. The organic light-emitting device according to claim 2, wherein the device emits blue light.

17. The indolo[3,2,1-jk]carbazole compound according to claim 1,
wherein the Ar is selected from the substituents listed in the formula [4] below:

[4]

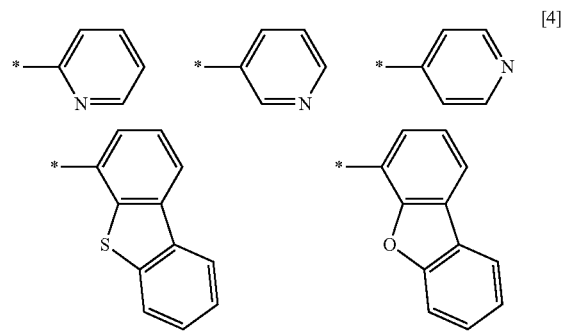

-continued
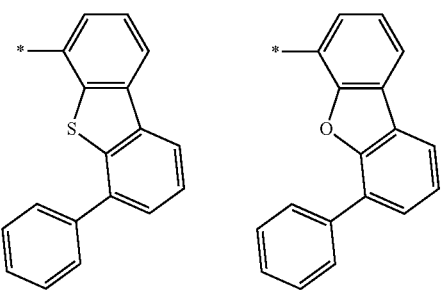
wherein * denotes a site to be bonded to the biphenyl group of the formula [1].
18. The indolo[3,2,1-jk]carbazole compound according to claim 1,
wherein the Ar is selected from the substituents listed in the formula [5] below:
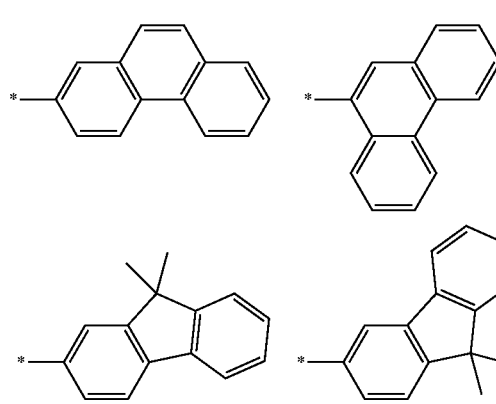
[5]
-continued
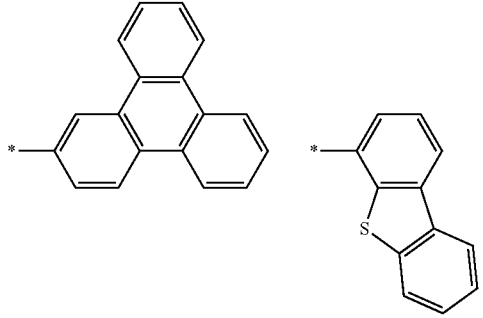
wherein * denotes a site to be bonded to the biphenyl group of the formula [1].
* * * * *